United States Patent
Koenig

(10) Patent No.: US 6,228,079 B1
(45) Date of Patent: *May 8, 2001

(54) METHOD AND APPARATUS FOR POWER MEASUREMENT IN RADIO FREQUENCY ELECTRO-SURGICAL GENERATORS

(75) Inventor: Franklin R. Koenig, Palo Alto, CA (US)

(73) Assignee: Somnus Medical Technology, Inc., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/167,505

(22) Filed: Oct. 6, 1998

Related U.S. Application Data

(60) Provisional application No. 60/062,543, filed on Oct. 6, 1997, provisional application No. 60/062,458, filed on Oct. 6, 1997, provisional application No. 60/061,193, filed on Oct. 6, 1997, provisional application No. 60/061,197, filed on Oct. 6, 1997, provisional application No. 60/061,714, filed on Oct. 6, 1997, and provisional application No. 60/061,213, filed on Oct. 6, 1997.

(51) Int. Cl.$^7$ .................................................. A61B 18/04
(52) U.S. Cl. ............................... 606/34; 606/32; 606/41; 606/42
(58) Field of Search .................................. 606/32, 34, 38, 606/41, 42, 46; 607/98, 101, 122

(56) References Cited

U.S. PATENT DOCUMENTS

| | | | |
|---|---|---|---|
| 5,233,515 | 8/1993 | Cosman | 364/413.02 |
| 5,318,563 | * 6/1994 | Malis et al. | 606/38 |
| 5,542,916 | * 8/1996 | Hirsch et al. | 604/22 |
| 5,769,847 | * 6/1998 | Panescu et al. | 606/42 |
| 5,871,481 | * 2/1999 | Kannenberg et al. | 606/34 |
| 5,906,614 | * 5/1999 | Stern et al. | 606/42 |

FOREIGN PATENT DOCUMENTS

WO 97/20510   6/1997   (WO) .............................. A61B/17/39

* cited by examiner

Primary Examiner—Michael Peffley
Assistant Examiner—David M. Ruddy
(74) Attorney, Agent, or Firm—Wilson Sonsini Goodrich & Rosati

(57) ABSTRACT

In an embodiment of the invention an apparatus for power measurement in an electro-surgical instrument is disclosed. The apparatus includes: sensors, a first summer and differencer, a peak detector, a second summer and differencer, and a multiplier. The sensors produce a voltage signal and a current signal proportional to a voltage and a current delivered by the first channel to the surgical site. The first summer and differencer sum the voltage signal together with the current signal to produce a first signal and difference the voltage signal with the current signal to produce a second signal. The peak detector couples to the first summer and differencer to form a third and a fourth signal proportional respectively to peak voltage levels in the first and the second signals. The second summer and differencer produce a fifth signal and a sixth signal proportional respectively to a difference and a sum of the third signal and the fourth signal. The multiplier multiplies the fifth and the sixth signals to produce a power signal equivalent to the actual power delivered by the first channel to the surgical site.

In another embodiment a waveform generator is disclosed which includes numerical values corresponding to sequential amplitude samples of a desired wave form. The waveform generator reads, at a time interval determined by a frequency of the oscillator, the numerical values to produce the oscillating signal with an amplitude proportionate to the numerical values.

7 Claims, 6 Drawing Sheets

METHOD AND APPARATUS FOR POWER MEASUREMENT IN RADIO FREQUENCY ELECTRO-SURGICAL GENERATORS

CROSS REFERENCE TO RELATED APPLICATION

This application claims the benefit of prior filed Provisional Application No. 60/062,543, filed on Oct. 6, 1997, entitled *Method And Apparatus For Power Measurement In Radio Frequency Electro-Surgical Generator*, Provisional Application No. 60/062,458, filed on Oct. 6, 1997, entitled *Linear Power Control With Digital Phase Lock*, Provisional Application, Provisional No. 60/061,193, filed on Oct. 6, 1997, entitled *Linear Power Control With PSK Regulation*, Provisional Application No. 60/061,197, filed on Oct. 6, 1997, entitled *Memory for Regulating Device Utilization and Behavior*, Provisional Application No. 60/061,714, filed on Oct. 6, 1997, entitled *Dual Processor Architecture For Electro Generator*, and Provisional Application No. 60/061,213, filed on Oct. 6, 1997, entitled *Method And Apparatus for Impedance Measurement In A Multi-Channel Electro-Surgical Generator*.

The present application is related to U.S. patent Application No. 09/167,217, filed Oct. 6, 1998, entitled *Linear Power Control With Digital Phase Lock*, U.S. patent application No. 09/167,412, filed Oct. 6, 1998, entitled *Liner Power Control With PSK Regulation*, U.S. patent application No. 09/167,222, filed Oct. 6, 1998, entitled *Memory for Regulating Device Utilization and Behavior*, U.S. patent application Ser. No. 09/167,508, filed Oct. 6, 1998, entitled *Dual Processor Architecture For Electro Generator*, U.S. patent application Ser. No. 09/167,215, filed Oct. 6, 1998, entitled *Method And Apparatus for Impedance Measurement In A Multi-Channel Electro-Surgical Generator*, International Application No. 41/821,065, filed Oct. 6, 1998, entitled *Linear Power Control With Digital Phase Lock*, and International Application No. 41/821,066, filed October 1998, entitled *Dual Processor Architecture For Electro Generator*.

Each of the above-cited applications is incorporated herein by reference in its entirety.

BACKGROUND OF THE INVENTION

I. Field of the Invention

This invention relates to the field of electro-surgical medical devices. More particularly, this invention relates to devices that deliver energy in the form of radio-frequency electrical current to tissue in order to perform surgical functions.

II. Description of Related Art

Various medical procedures rely on high-frequency electrical currents to deposit energy and thus heat human and animal tissues. During such procedures, a high-frequency current is passed through the tissue between electrodes. One electrode is located at the tip of a surgical probe. Another electrode is located elsewhere, and may be a grounding pad or another surgical probe tip. The tissue to be treated lies between the electrodes.

When the electrode circuit is energized, the electric potential of the electrodes at the probe tips oscillates at radio frequencies about a reference potential. If one is used, a grounding pad remains at a floating reference potential. As the electric potential of the probe electrodes varies, a motive force on charged particles in the tissue is established that is proportional to the gradient of the electric potential. This electromotive force causes a net flow of electric charge, a current, to flow from one electrode, through the tissue, to any other electrode(s) at a lower potential. In the course of their flow, the charged particles collide with tissue molecules and atoms. This process acts to convert electrical energy to sensible heat in the tissue and is termed Joule heating.

Upon heating, surgical functions such as cutting, cauterizing and tissue destruction can be accomplished. For example, tissues can be cut by heating and eventually vaporizing the tissue cell fluids. The vaporization causes the cell walls to rupture and the tissue to cleave. When it is beneficial to destroy tissue, comparatively higher rates of energy deposition can cause tissue ablation.

Ablation of cellular tissues in situ is used in the treatment of many diseases and medical conditions either alone or combined with surgical removal procedures. Surgical ablation is often less traumatic than surgical removal procedures and may be the only alternative where other procedures are unsafe.

Tissue ablation devices commonly utilize electromagnetic (microwave, radio frequency (RF), lasers) or mechanical (acoustic) energy. In the category of electro-surgical devices, microwave ablation systems utilize a microwave antenna which is inserted into a natural body opening through a duct to the zone of treatment. Electromagnetic energy then radiates from the antenna through the duct wall into the target tissue. However, there is often severe trauma to the duct wall in this procedure since there is a significant microwave energy flux in the vicinity of the intended target. The energy deposition is not sufficiently localized. To reduce this trauma, many microwave ablation devices use a cooling system. However, such a cooling system complicates the device and makes it bulky. Laser ablation devices also suffer the same drawback as microwave systems. The energy flux near the target site, while insufficient to ablate the tissue, is sufficient to cause trauma.

Application of RF electric currents emanating from electrode tips offers the advantage of greater localization of the energy deposition since the electrode tip is nearly a point source. However, these devices require consideration and monitoring of the power applied to the tissue as well as the tissue response. Since the electric energy flux is localized, the electrical dissipation and storage characteristics of the tissue carrying the current may vary with time as a result of the current-induced heating. As a result, the power absorbed by the tissue as heat could vary over the time of treatment due to changing values of the tissue's electrical properties.

In addition, the localization of energy flux in an RF electro-surgical device may require a number of electrodes to be included in the surgical probe to provide adequate area coverage. With multiple electrodes in a surgical probe, each probe electrode may not be at the same electric potential at each instant due to amplitude, frequency or phase variations in their RF oscillations. In this case, an electric current would flow between the probe electrodes, coupling them to an extent primarily determined by the difference in electric potential between the electrodes and the electrical properties of the tissue between the electrode tips. Thus, the power may be delivered across several electrodes.

As described, electric power determination is critical in each electrode circuit of an RF electro-surgical device since it is directly related to the intended medical effects. Prior art approaches for determining the power on an electrode circuit utilize high speed analog multipliers to multiply measured current and voltage signals. A drawback to these approaches is that high speed, high-precision analog multipliers and associated root mean square (RMS) converters are expensive.

Prior art methods for RF waveform synthesis in electro-surgical devices often produce square waveforms repeating at radio frequencies. This approach, however, has the drawback that substantial filtering must be applied to remove the high-frequency Fourier components of the RF squarewave. This is necessary to comply with FCC regulations on emitters. The required filtering, typically achieved with a resonant inductor-capacitor (LC) circuit, degrades the control of the relative voltages at the electrode tips by requiring a sharp bandpass filter (a filter with high quality factor, Q). With a high Q filter, small differential variations in the tuning of the electrode channels (due, for example, to aging of the capacitors and inductors) lead to differential voltages at the electrode tips. As described, this can confuse monitoring of the power applied to the surgical site by inducing electrode coupling, termed cross-talk. Therefore, to improve control of the electric power applied to the patient, there is a need in the field for an improved method and apparatus for power measurement and radio frequency waveform synthesis in electro-surgical generators.

SUMMARY OF THE INVENTION

A method and apparatus for power measurement and radio frequency waveform synthesis in electro-surgical generators is disclosed.

In an embodiment of the invention an apparatus for power measurement in an electro-surgical instrument is disclosed. The electro-surgical instrument includes a first channel for delivery of energy to a surgical site. The apparatus for power measurement includes: sensors, a first summer and differencer, a peak detector, a second summer and differencer, and a multiplier. The sensors produce a voltage signal and a current signal proportional to a voltage and a current delivered by the first channel to the surgical site. The first summer and differencer sum the voltage signal together with the current signal to produce a first signal and difference the voltage signal with the current signal to produce a second signal. The peak detector couples to the first summer and differencer to form a third and a fourth signal proportional respectively to peak voltage levels in the first and the second signals. The second summer and differencer produce a fifth signal and a sixth signal proportional respectively to a difference and a sum of the third signal and the fourth signal. The multiplier multiplies the fifth and the sixth signals to produce a power signal equivalent to the actual power delivered by the first channel to the surgical site.

In an embodiment of the invention a method for power measurement in an electro-surgical instrument is disclosed. The method for power measurement comprises the acts of:
  generating a first signal and a second signal proportional respectively to a sum and a difference of a current and a voltage delivered by the first channel to the surgical site;
  forming a third and a fourth signal proportional respectively to peak voltage levels in the first and the second signals;
  producing a fifth signal and a sixth signal proportional respectively to a difference and a sum of the third signal and the fourth signal;
  multiplying the fifth and the sixth signals to produce a power signal equivalent to the actual power delivered by the first channel to the surgical site.

In another embodiment of the invention an apparatus for signal generation in an electro-surgical instrument is disclosed. The electro-surgical instrument includes a first channel for delivery of energy in the form of an oscillating signal to a surgical site. The apparatus for signal generation includes an oscillator a waveform generator, a power measurement circuit and a controller. The waveform generator includes numerical values corresponding to sequential amplitude samples of a desired wave form. The waveform generator is coupled to the oscillator. The waveform generator reads, at a time interval determined by a frequency of the oscillator, the numerical values to produce the oscillating signal with an amplitude proportionate to the numerical values. The power measurement circuit determines a difference between the actual power delivered by the first channel to the surgical site and a target power. The controller varies the magnitude of the oscillating signal proportionate to the difference between the actual power and the target power.

In another embodiment of the invention an apparatus for signal generation includes multi-channel capability.

In another embodiment of the invention a method for signal generation in an electro-surgical instrument is disclosed. The electro-surgical instrument includes a first channel for delivery of energy in the form of an oscillating signal to a surgical site. The method for signal generation comprising the acts of:
  storing numerical values corresponding to sequential amplitude samples of a desired wave form;
  reading at set time intervals the numerical values stored in said storing act to produce the oscillating signal with an amplitude proportionate to the values stored in said storing act;
  determining a difference between the actual power delivered by the first channel to the surgical site and a target power; and
  varying the magnitude of the oscillating signal proportionate to the difference between the actual power and the target power.

In another embodiment of the invention a multi-channel method for signal generation is disclosed.

BRIEF DESCRIPTION OF THE FIGURES

The above and other objects and advantages of the invention will be apparent upon consideration of the following detailed description, taken in conjunction with the accompanying drawings, in which like reference numerals refer to like parts throughout.

DETAILED DESCRIPTION

Figure 1:
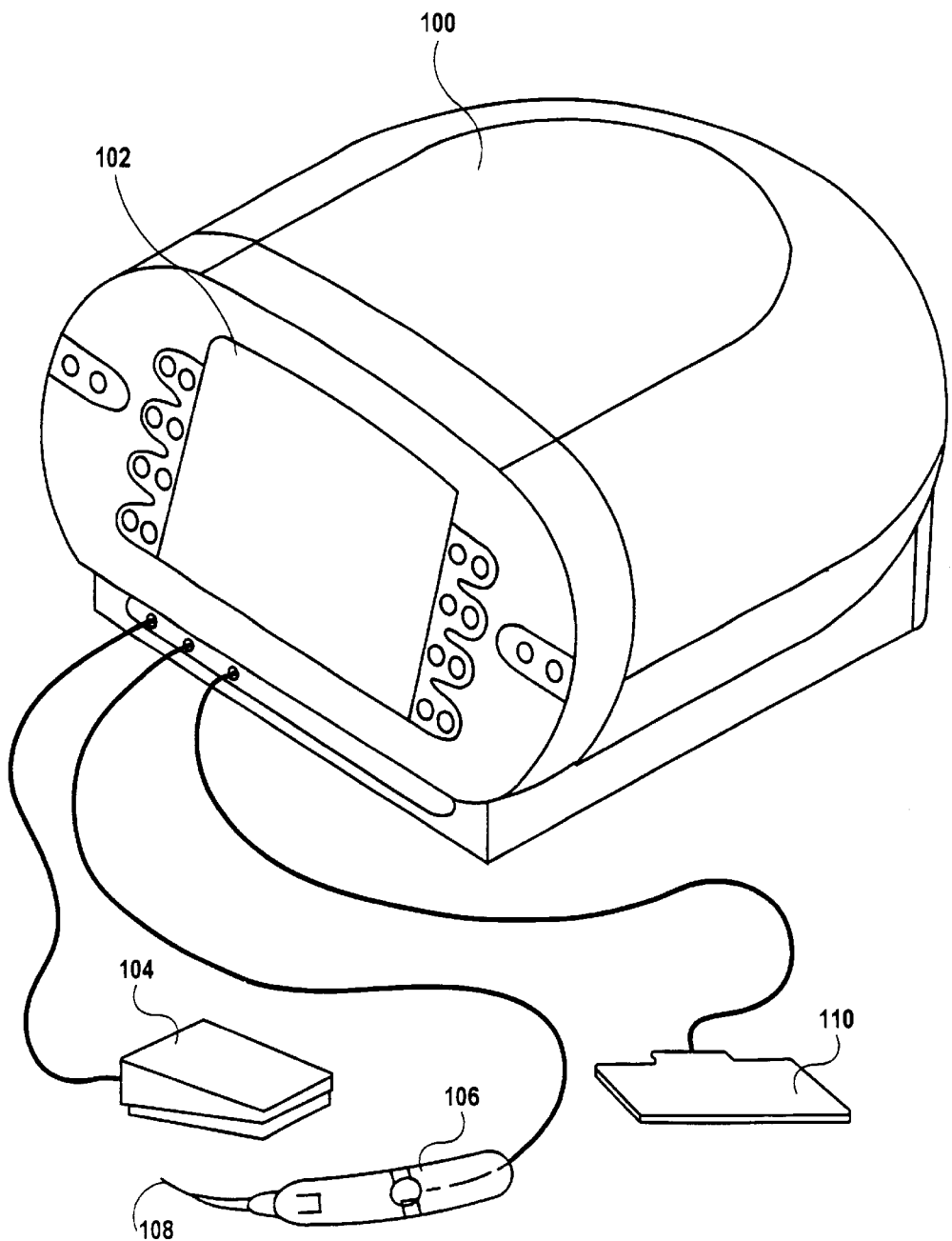
FIG. 1 shows the apparatus for a typical embodiment of the RF electro-surgical device.

FIG. 1 shows the apparatus for a typical embodiment of the RF electro-surgical device. The system comprises an RF power supply 100 with a user input and display panel 102, a foot switch 104, a surgical handset 106 with a surgical probe 108 and an electrical grounding pad 110.

The RF power supply 100 converts the low frequency electrical energy supplied by a wall connection (not shown) into the high frequency or RF energy necessary for surgery.

The user input and display panel 102 displays relevant parameters and provides buttons and switches for user input to the control systems. The foot switch 104 connected to the power supply provides means for switching the unit on and off. The surgical handset 106 is also connected to the power supply and is the means for delivering the RF energy to the surgical probe 108. The probe has one or more electrodes. The electrical grounding pad 110 is also connected to the power supply and is at a floating reference potential. Some embodiments of this invention do not have an electrical grounding pad.

Figure 2:
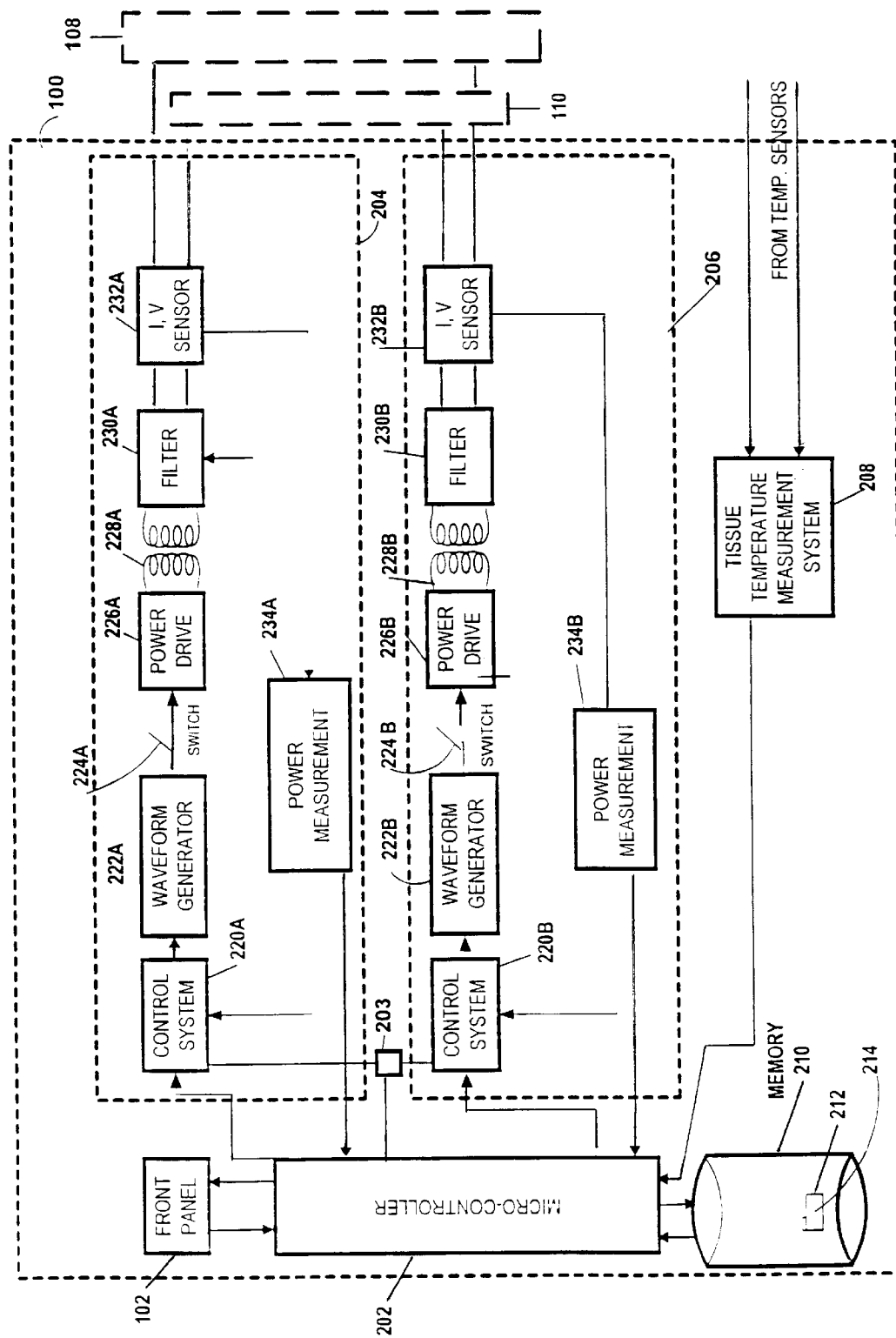
FIG. 2 shows a block diagram showing elements of the system hardware architecture.

FIG. 2 is a block diagram showing elements of the system hardware architecture showing a block diagram of the RF power supply 100, surgical probe 108 and grounding pad 110. Within the power supply, the user input and display panel 102, micro controller 202, RF oscillator 203, first and second electrode channels 204 and 206, temperature measurement system 208, memory unit 210 and power/temperature schedule 212 are indicated. Electrode channels 204 and 206 are identical, each comprising a control systems 220A–B, waveform generator 222A–B, an isolation switch 224A–B, a power drive 226A–B, a transformer 228A–D, a filter 230A–B, current and voltage sensors 232A–B, and power measurement systems 234A–B.

In FIG. 2, the user input and display panel 102 is connected to the micro-controller 202 which is connected to the memory unit 210 comprising power/temperature schedule 212. The micro-controller is connected with the identical electrode channels 204–206 and also to the tissue temperature measurement system 208. Within each electrode channel, the control systems 220A–B are connected to the micro-controller as well as the tissue temperature measurement system. The control system also connects to the waveform generators 222A–B and the common RF oscillator 203. The waveform generators are connected to the power drive 226A–B through the isolation switches 224A–B. It is obvious to a person skilled in the art that the swithching can be accomplished at locations other than shown in FIG. 2 including the micro-controller, power drive, filter and the electrode. The RF signals from the transformer 228A–B feed into filters 230A–B. The current and voltage sensors 232A–B connect to the filter, grounding pad 10, surgical probe 108 and the power measurement systems 234A–B.

The micro-controller 202 implements control programs and logic contained in power/temperature schedule 212, provides an input to the control system as to the desired values for time scales and power or temperature levels for the surgical procedures to be performed. To act as a means for control, the micro-controller is in two way communication with the user through the user input and display panel 102 as well as receives input from the power and tissue temperature measurement systems 234A–B, 208A–B. Control variables are passed to hardware control systems 220A–B to achieve the desired amplitude and frequency of the RF electric currents. The waveform generator 222A–B generates RF oscillations that modulate the output of the power drive 226A–B. Power is coupled through transformer 228A–B by the principle of induction, isolating the patient from direct current (DC). Further frequency filtering is accomplished by filter 230A–B. Current and voltage sensors 232A–B provide required signals for the power measurement systems 234A–B to determine the actual power transferred to the tissue by the current passing from surgical probe 108 to grounding pad 110. Once the actual power is determined in the power measurement systems 234A–B the results are passed to micro-controller 202 and control system 220A–B. The micro-controller compares the actual power to the desired power level and obtains the difference between the two. In other embodiments, this is accomplished by analog hardware in control system 220A–B. In this alternate embodiment the micro-controller downloads new target values to the control system 220A–B. The control system 220A–B uses these new values as well as power measurements performed by the power measurement system 234A–B to adjust the drive level to the waveform generators 222A–B so as to minimize the error between target power and actual power delivered by the channels. If the actual power is less than the desired power, a.k.a. target power, then the drive level of either or both the waveform generator(s) 222A–B and/or the power drives 226A–B is increased. Conversely if the actual power is greater than the desired power then the drive level of either or both the waveform generator(s) and/or the power drives is decreased.

In an embodiment of the invention the target power is fixed over the course of the operation. In another embodiment of the invention the control parameters for the operation vary as a function of time. That schedule of power or temperature as a function of time is recorded in memory unit 210 and specifically the power/temperature schedule 212. During the course of the surgical operation the micro-controller will update target parameters, e.g. power or temperature, using the power/temperature schedule and an internal timer which is initialized at the start of surgery. Thus the micro-controller periodically updates power/temperature targets on the basis of the data stored in the power/temperature schedule. These target levels are compared with actual power levels and the micro-controller 202 adjusts the drive level of either or both channels 204–206 to reduce the difference between the actual power and the target power. In another embodiment, the adjustment is made by analog hardware in control system 220A–B. In another embodiment of the invention in which the power/temperature schedule contains only target temperatures the micro-controller uses the actual power measurements to adjust drive levels so as to maintain target temperatures at the surgical site.

Figure 3:
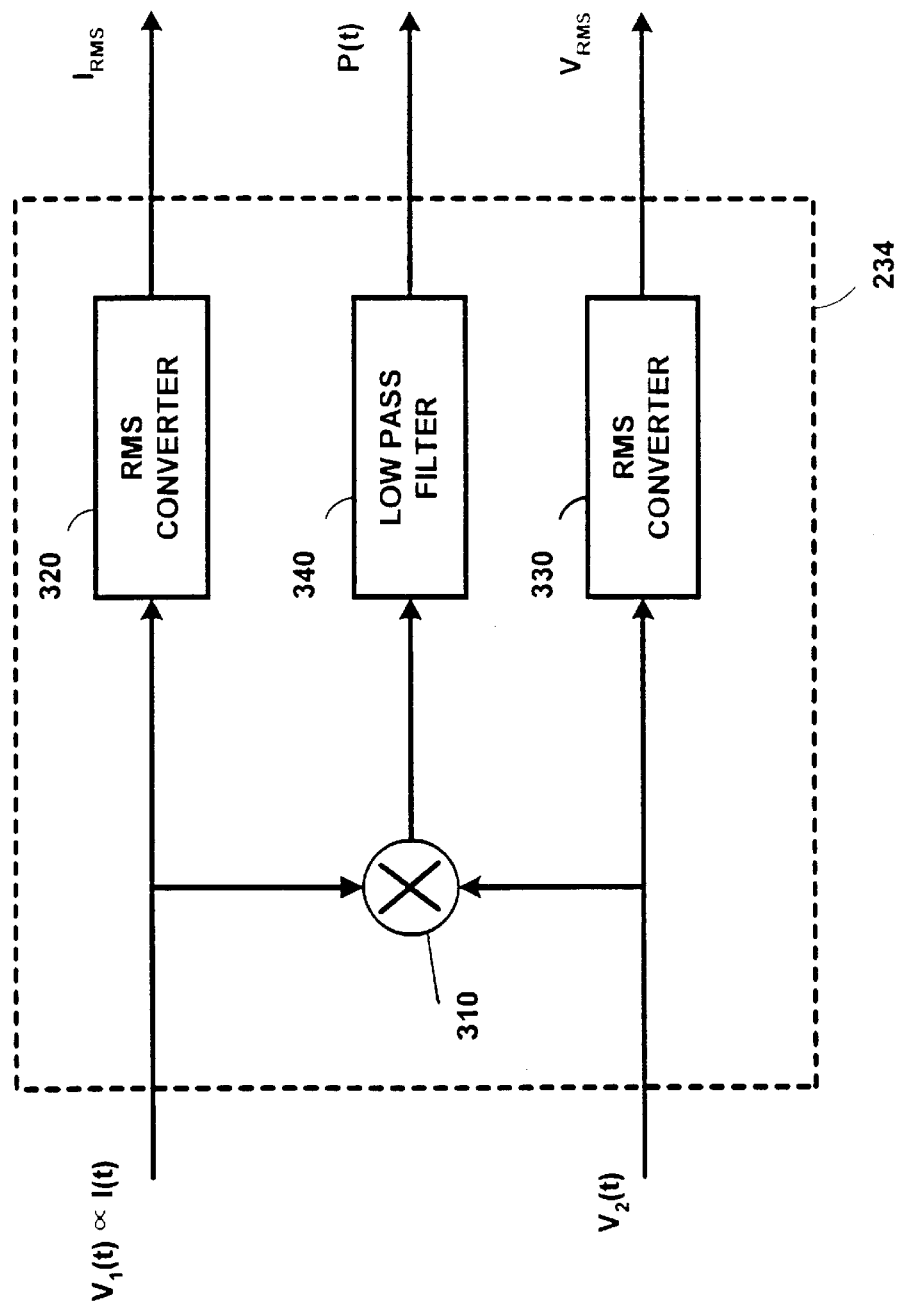
FIG. 3 shows a prior art power measurement system.

FIG. 3 is a prior art electric power measurement system 234. This system includes a a high speed analog multiplier 310, and RMS converters 320 and 330, and a low pass filter 340.

In FIG. 3, high speed analog multiplier 310 multiplies input voltages. One voltage represents the electric potential difference across the electrode channel and another voltage is proportional to the current flowing through the patient on that channel. The product of these voltages is proportional to and represents the instantaneous power being delivered to the patient. Low pass filter 340 filters the instantaneous power signal to provide a signal representative of the average power delivered to the patient on that channel. This is the quantity of interest to the medical practitioner. RMS converters 320 and 330 transform their respective RF inputs into slowly varying signals that represent the root mean square values of the current and voltage being delivered to the patient. The chief disadvantage of the prior art approach in FIG. 3 is that it requires the use expensive components such as a high speed, high precision analog multiplier and high speed RMS converters.

Figure 4:
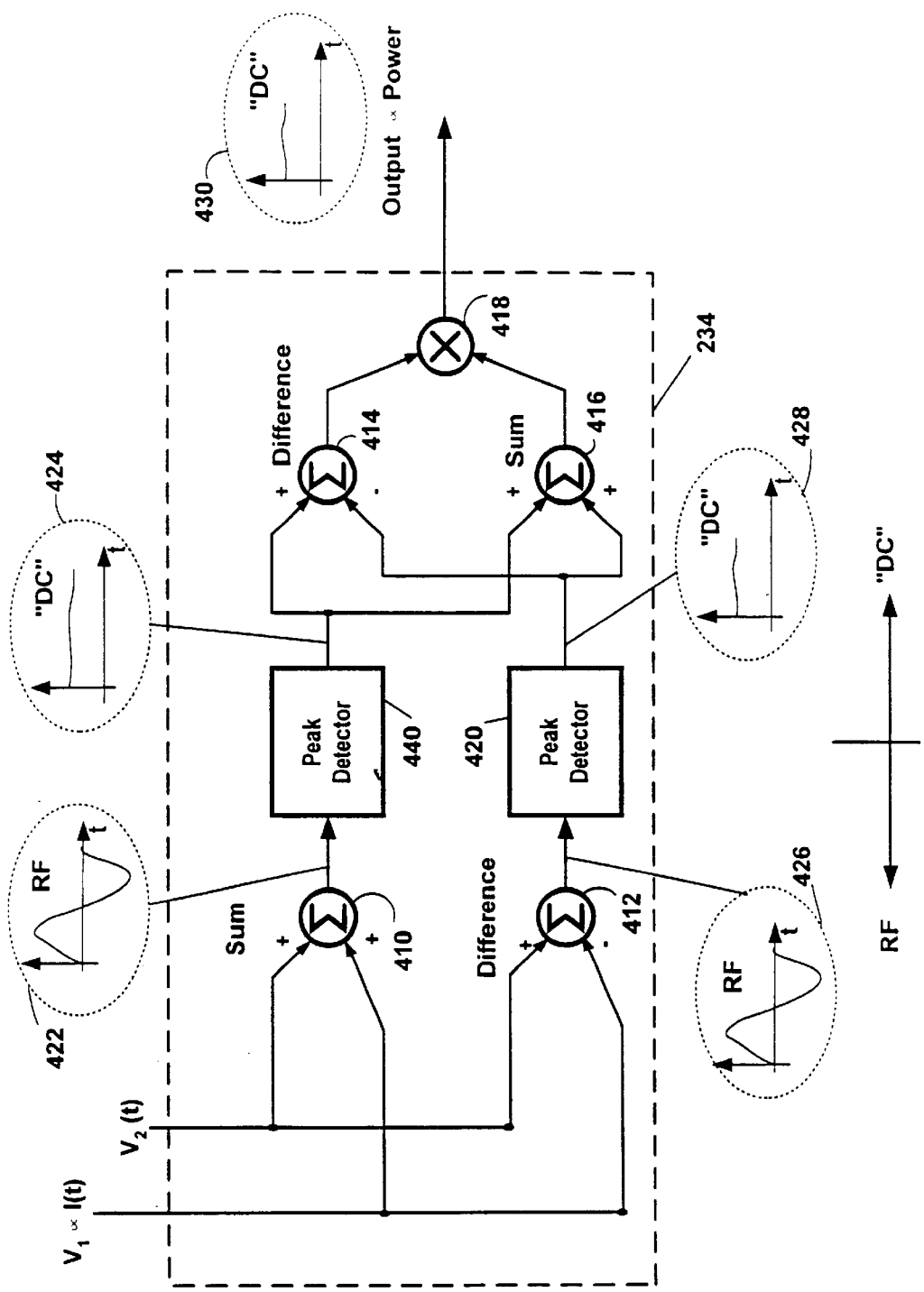
FIG. 4 shows the preferred embodiment of the current invention.

FIG. 4 shows the power measurement system 234 of the preferred embodiment of this invention. The chief advantage of this embodiment is that it does not require the use of a high speed analog multiplier. It can use a much less expensive low speed precision analog multiplier. It also does not require the use of RMS converters. However, to retain accuracy, it requires the input signals to be sinusoidal.

The embodiment illustrated in FIG. 4 consists of summing amplifier 410 and differencing amplifier 412, i.e. the first summer and differencer; peak detectors 420–440; summing amplifier 416 and differencing amplifiers 414, i.e. the second summer and differencer, and low speed analog multiplier 418.

The inputs to the system in FIG. 4 are voltage and current signals from sensors 232A–B (See FIG. 2) that represent the instantaneous voltage and instantaneous current in a channel of the loaded circuit In the current embodiment of the invention the input current and voltage signals are high frequency sinusoidal waveforms, with negligible DC offset.

Summing amplifier 410 produces a voltage 422 that is the sum of the current and voltage signals and oscillates at radio frequencies. Similarly, differencing amplifier 412 produces a voltage 426 which represents the difference of the current and voltage signals and oscillates at radio frequencies. The output of summing amplifier 410 feeds into peak detector 440 which transforms the input into a slowly varying voltage 424 that is representative of the peak amplitudes of the sinusoid from summing amplifier 410. Similarly, peak detector 420 produces a slowly varying voltage 428 that is representative of the peak amplitude of the sinusoid from summing amplifier 412. It can be readily appreciated that the proportionality of the time integrals of the signals from the peak detectors and those of their inputs is preserved if the inputs have an invariant waveform, e.g. sinusoidal.

Summing amplifier 416 and differencing amplifier 414 are low speed devices. They accept as inputs the "DC", e.g. steady state, outputs of peak detectors 440 and 420. Differencer 414 produces an output signal proportional to the difference in the outputs of peak detectors 440 and 420. Summer 416 produces an output signal that is proportional to the sum of the outputs of the peak detectors. The outputs of summing amplifier 416 and differencing amplifier 414 are multiplied by low speed analog multiplier 418 to produce a voltage that is proportional to the actual power applied on the channel to the load. This power output signal can be converted to one which is equivalent, as opposed to proportional, to the actual power by applying a coefficient to the multiplication process performed by low speed analog multiplier 418. Note that the power output signal is proportional to the non-reactive component of power, a.k.a. actual power or true power. This non-reactive component represents the electric power absorbed by the tissue in a medical procedure.

Electric power determination enables feedback control of a power delivery system. For consistency with the method of power determination, the method of RF waveform synthesis of this invention delivers sinusoidally varying power to each electrode channel.

Figure 5:
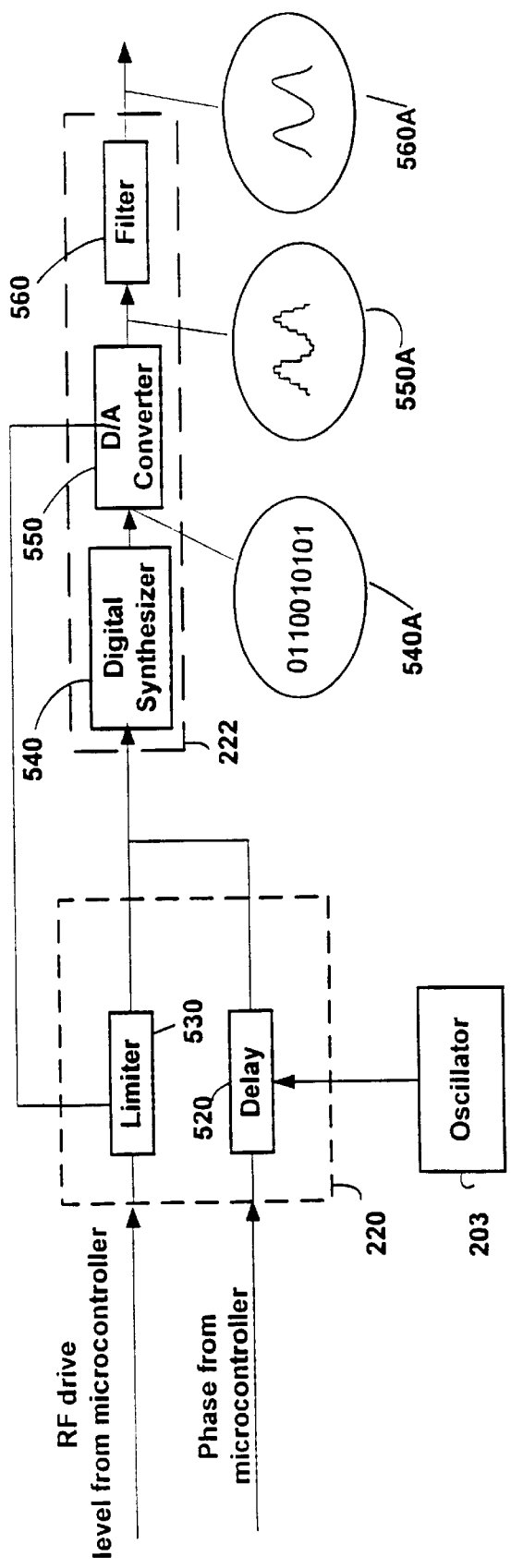
FIG. 5 shows a schematic of the electric power determination system for a single electrode channel.

FIG. 5 is a schematic of the RF waveform synthesis system for a single electrode channel showing the control system 220 and waveform generator 222 (see FIG. 2) and RF oscillator 203. In FIG. 5, the control system is comprised of adjustable delay generator 520 and RF drive level limiter 530. The waveform generator 222 comprises a digital synthesizer 540, digital-to-analog converter 550 and filter 560.

The control system 220 shown in FIG. 5 receives input from the RF master oscillator and micro-controller 202 (see FIG. 2). The micro-controller provides the RF drive level and a phase-controlling signal. Phase input from the micro-controller and input from the RF oscillator is processed by adjustable delay generator 520. Output from the delay generator is passed to the waveform generator 222 as is the RF drive level, after passing limiter 530.

The RF oscillator 203 provides a time base for the control system. The adjustable delay generator 520, along with the input phase data from the micro-controller allow a controllable phase difference in the power applied over different electrode channels in a multi-channel device. The limiter 530 serves to prevent a predetermined RF drive level from being exceeded. The phase information from the control system is passed to the digital synthesizer 540 which, acting with a stored look-up table, sends a time series of binary digits, e.g. 540A, to the digital-to-analog (D/A) converter 550. The output of the D/A converter is an analog waveform, e.g. 550A. Filter 560 creates a clean sinusoid, e.g. 560A, from this signal by filtering out the higher frequency components of the waveform, as shown in FIG. 5.

Figure 6:
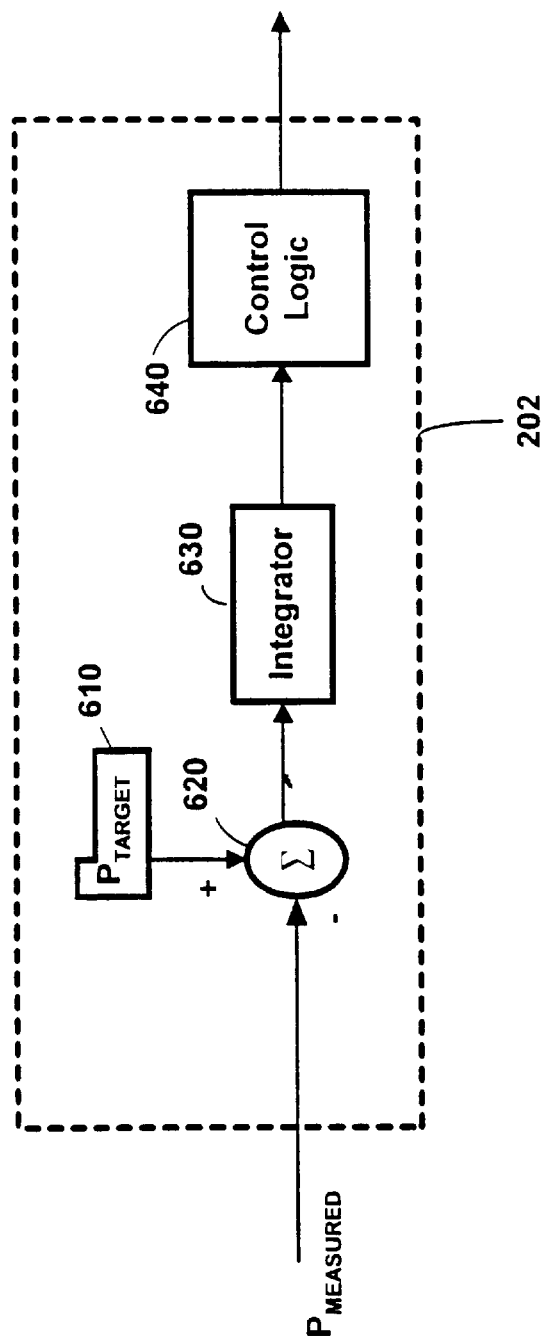
FIG. 6 shows the generation of the control system feedback.

FIG. 6 shows the process for generating the control system feedback in the micro-controller 202. In FIG. 6, the power determined by direct measurement of the electrode voltage and current in the power measurement system 234 (see FIG. 2, FIG. 4) is compared to the target power schedule 610 in differencing element 620. The resulting difference is integrated over an adjustable time by integrating element 630. Control logic 640 is implemented to drive the difference between the target power and the power determined by measurement to zero by adjusting the micro-controller output that is sent to the control system 220.

Although the foregoing invention has been described in detail for purposes of clarity of understanding, it will be obvious that certain modifications may be practiced within the scope of the appended claims.

What is claimed is:

1. A method for signal generation in an electro-surgical instrument including a first channel and a second channel for delivery of energy in the form of a first oscillating signal and a second oscillating signal to a surgical site, and the method for signal generation comprising the acts of:

storing numerical values corresponding to sequential amplitude samples of a desired wave form;

reading at set time intervals the numerical values stored in said storing act to produce a first oscillating signal and a second oscillating signal each with an amplitude proportionate to the values stored in said storing act;

delaying the reading of the numerical values associated with first oscillating signal to introduce a phase shift of the first oscillating signal with respect the second oscillating signal;

determining a difference between the actual power delivered by the first channel to the surgical site and a target power; and varying a magnitude of the first oscillating signal and the second oscillating signal proportionate to the difference between the actual power and the target power.

2. The method of claim 1, wherein the reading act further comprises the acts of:

converting the numerical values to an analog waveform; and smoothing the analog waveform to produce the first oscillating signal and the second oscillating signal.

3. The method of claim 2, wherein the smoothing act further comprises the act of:

filtering the analog waveform to interpolate smoothly between the numerical values stored in said storing act.

4. The method of claim 1 further comprising the acts of:

limiting the magnitude of the first oscillating signal and the second oscillating signal.

5. An apparatus for signal generation in an electro-surgical instrument including a first channel and a second channel for delivery of energy in the form of a first oscillating signal and a second oscillating signal to a surgical site, and the apparatus for signal generation comprising:

an oscillator;

a waveform generator including numerical values corresponding to sequential amplitude samples of a desired wave form, and the waveform generator coupled to the oscillator and reading at a time interval determined by a frequency of the oscillator the numerical values to produce a first oscillating signal and a second oscillating signal each with an amplitude proportionate to the numerical values;

a power measurement circuit to determine a difference between the actual power delivered by the first channel to the surgical site and a target power;

a delay to delay the reading of the numerical values associated with the first oscillating signal to introduce a phase shift of the first oscillating signal with respect the second oscillating signal; and a controller to vary a magnitude of the first oscillating signal and the second oscillating signal proportionate to the difference between the actual power and the target power.

6. The apparatus of claim 5, wherein the waveform generator further comprises:

a digital synthesizer for generating the numerical values;

a convertor for converting the numerical values generated by the digital synthesizer to analog waveform; and a filter to smooth the analog waveform to produce the first oscillating signal and the second oscillating signal.

7. The apparatus of claim 5 further comprising:

a limiter to limit the magnitude of the first oscillating signal and the second oscillating signal.

* * * * *